(12) United States Patent
Finehout et al.

(10) Patent No.: US 9,714,447 B2
(45) Date of Patent: Jul. 25, 2017

(54) DETECTION OF NUCLEIC ACID AMPLIFICATION IN A POROUS SUBSTRATE

(71) Applicant: General Electric Company, Schenectady, NY (US)

(72) Inventors: Erin Jean Finehout, Clifton Park, NY (US); Christopher Michael Puleo, Niskayuna, NY (US); Ralf Lenigk, Schenectady, NY (US); Jason M. Nichols, Schenectady, NY (US); John Nelson, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 105 days.

(21) Appl. No.: 13/970,315

(22) Filed: Aug. 19, 2013

(65) Prior Publication Data
US 2015/0050654 A1    Feb. 19, 2015

(51) Int. Cl.
*C12Q 1/68* (2006.01)

(52) U.S. Cl.
CPC ......... *C12Q 1/6844* (2013.01); *C12Q 1/6816* (2013.01); *C12Q 1/6851* (2013.01)

(58) Field of Classification Search
None
See application file for complete search history.

(56) References Cited

U.S. PATENT DOCUMENTS 5,853,990 A    12/1998 Winger et al.
6,649,378 B1 *  11/2003 Kozwich ............... B01L 3/502
                                              422/68.1

| 2002/0123062 | A1 | 9/2002 | Wittwer |
| 2003/0165898 | A1 | 9/2003 | Todd |
| 2006/0035231 | A1 | 2/2006 | Van Beuningen et al. |
| 2008/0280285 | A1 * | 11/2008 | Chen ............... B01L 3/502715 435/5 |
| 2009/0203083 | A1 | 8/2009 | Mauritz |

(Continued)

FOREIGN PATENT DOCUMENTS

| WO | 2004099438 A1 | 11/2004 |
| WO | 2006041524 A2 | 4/2006 |
| WO | 2009000764 A2 | 12/2008 |

(Continued)

OTHER PUBLICATIONS

Chen et al. (2010) Biomed Microdevices vol. 12: 705-719 DOI 10.1007/s10544-010-9423-4.*

(Continued)

*Primary Examiner* — Samuel Woolwine
(74) *Attorney, Agent, or Firm* — Pabitra K. Chakrabarti (57) ABSTRACT

The present disclosure relates to characterization of biological samples by amplification detection in a porous substrate. By way of example, a porous substrate may include amplification reagents configured to provide a signal when released during amplification. When a sample is applied, amplification occurs as a wavefront from the application point, and the time that the wavefront reaches a distance on the porous substrate is related to an initial concentration of the sample applied. By detecting the distance traveled by the amplification products at one or more time points, an initial concentration of the sample may be estimated.

23 Claims, 7 Drawing Sheets

(56) References Cited

U.S. PATENT DOCUMENTS

2010/0173290 A1  7/2010  Prins

FOREIGN PATENT DOCUMENTS

WO  2009080817 A2  7/2009
WO  2013080154 A1  6/2013

OTHER PUBLICATIONS

Dudek et al. (2010) Anal. Chem vol. 82: 2029-2035.*
Sood et al. (2005) J Am. Chem. Soc. vol. 127 (8) pp. 2394-2395 DOI: 10.1021/ja043595x.*
Higuchi et al., "Simultaneous Amplification and Detection of Specific DNA Sequences", Nature Biotechnology, pp. 413-417, vol. 10, 1992.
Fang et al., "Loop-Mediated Isothermal Amplification Integrated on Microfluidic Chips for Point-of-Care Quantitative Detection of Pathogens", Analytical chemistry, pp. 3002-3006, vol. 82, Issue 7, 2010.
Gandelman et al., "Novel Bioluminescent Quantitative Detection of Nucleic Acid Amplification in Real-Time", PLoS One, pp. 1, vol. 5, Issue 11, Nov. 2010.
ISA/210, International Search Report, PCT/EP2014/067685; mailed Nov. 11, 2014; 2 pages.

* cited by examiner

Speed of reaction front ∝ Initial biomolecule concentration

DETECTION OF NUCLEIC ACID AMPLIFICATION IN A POROUS SUBSTRATE

STATEMENT REGARDING FEDERALLY SPONSORED RESEARCH & DEVELOPMENT

This invention was made with Government support under contract number HR0011-11-C0127 awarded by the Defense Advanced Research Projects Agency. The Government has certain rights in the invention.

BACKGROUND

The subject matter disclosed herein relates to nucleic acid amplification in a porous substrate.

Caregivers may use diagnostic tests to determine if a patient has a particular clinical condition. Such tests may be performed by testing a patient sample (e.g., blood or urine) for the presence of one or more markers such as proteins or small molecules and, depending on their complexity, the tests may be performed in a dedicated testing laboratory or at the point of care, e.g., in the doctor's office or in the field. However, in certain circumstances, a diagnostic test may be a test for the presence of a particular nucleic acid sequence, either sequences in the patient's own genetic material or sequences associated with pathogenic infection. Relative to proteins or small molecule markers, a given nucleic acid sequence may be present in relatively low concentrations in a given biological sample. Accordingly, many techniques for assessing the presence or concentration of a nucleic acid sequence of interest rely on amplification techniques that enrich the sample by amplifying the sequence of interest. For example, nucleic acid testing may be performed via PCR-based amplification techniques, which are relatively complex and are typically performed by skilled technicians using specialized devices.

BRIEF DESCRIPTION

In one embodiment, a method of assessing amplification of nucleic acids is provided. The method includes providing a porous substrate comprising a plurality of amplification reagents distributed throughout the porous substrate; applying a sample comprising nucleic acids to a predetermined initial location on the porous substrate; allowing the sample to react with the amplification reagents on the porous substrate for a duration of time to generate amplification products of a nucleic acid sequence of interest, wherein amplification products comprise one or more detectable moieties configured to provide a signal when the amplification products are generated during amplification; and determining an initial concentration of the sample based on a time-dependent progress of the signal within the substrate.

In another embodiment, an amplification system includes a porous substrate; a plurality of amplification reagents comprising one or signal molecules configured to provide a detectable moiety during amplification distributed throughout the porous substrate and one or more primers complementary to a target nucleic acid sequence; a detector configured to detect the moiety at a plurality of locations on the porous substrate and provide an output related to the detected signal at the respective plurality of locations; and a processor configured to receive the output and determine an initial concentration of the target nucleic acid sequence applied to the porous substrate based on a farthest distance from a sample application point on the porous substrate in which the signal is above a threshold or a time the signal is above threshold at a specified distance from the sample application point on the porous substrate.

In another embodiment, a method includes providing a porous substrate comprising a plurality of amplification reagents distributed throughout the porous substrate, wherein the amplification reagents comprise one or more signal molecules configured to provide a signal during amplification and one or more primers complementary to a target nucleic acid sequence and a sample comprising a known starting copy number for the target nucleic acid sequence to an initial location on a porous substrate; and determining a farthest distance from the initial location in which the signal is above a threshold at a plurality of time points.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Paper diagnostics are of growing interest to those that design, sell, and use point-of-care platforms. Such diagnostics may be low-cost, portable, and easy to use. For example, paper diagnostics have been used to detect proteins or small molecules. Implementation of paper diagnostic techniques for nucleic acid amplification is more complex. Certain techniques may involve amplification via a paper platform, but a separate end-point detection of the amplified products, e.g., by flowing the amplified material over a capture line. Accordingly, such techniques involve more steps and user effort relative to a paper diagnostics used for protein detection. Further, certain techniques measure change in relative intensity over time, which requires a detector with a wide dynamic range to achieve a large range of quantitation. Provided herein are techniques that may be used to amplify and detect nucleic acids in real-time in a biological sample using a paper or porous solid substrate. The disclosed embodiments may be used to detect a presence of a nucleic acid sequence of interest in a biological sample. Further, in certain embodiments, the amount of starting sequence in the sample may be quantified based on a detected distance traveled by the amplification products in the porous substrate over time. In another embodiment, the quantification metrics (e.g., velocity vs. time, Vmax) of the amplified products may be used as a quality control. As noted, by providing amplification and detection in a single substrate, the present techniques eliminate the steps of removing the amplification products from the substrate before detection. Accordingly, amplification and detection via a porous substrate as provided may be faster and more convenient and, thus, may be performed at the point of care or may improve workflow in a dedicated testing laboratory. Further, by only measuring when the signal goes above a threshold, the present techniques can achieve a large dynamic range of quantitation by using a detector with a small dynamic range.

Although the disclosed embodiments are generally disclosed in the context of nucleic acids, it should be understood that other self-amplifying components may be tested as provided herein. Further, the nucleic acids disclosed herein may include DNA or RNA, and may be in the form of purified nucleic acids, unprocessed biological fluids that include nucleic acids or partially processed biological fluids or samples, bacterial samples, pathogenic samples, environmental samples etc. A "sample" or "biological sample" may include samples taken from biological subject, including biological tissue or fluid obtained from a subject. Such samples can be, but are not limited to, body fluid (e.g., blood, blood plasma, serum, or urine), organs, tissues, biopsies, fractions, and cells isolated from, or located in, any biological system, such as mammals. Biological samples also may include sections of the biological sample including tissues (e.g., sectional portions of an organ or tissue). Biological samples may also include extracts from a biological sample, for example, nucleic acids purified from a biological fluid (e.g., blood or urine). Samples may also include unprocessed bodily fluids. For example, in one embodiment, it is envisioned that unprocessed bodily fluids may be applied directly to the porous substrate without any processing. In addition, the techniques may also be used to assess the presence of nucleic acids of interest in environmental samples, including forensic or security screening samples. In one embodiment, the techniques may be used to determine if a particular environment (e.g., a filtering system, a piping system) has been contaminated with one or more pathogens.

Figure 1:
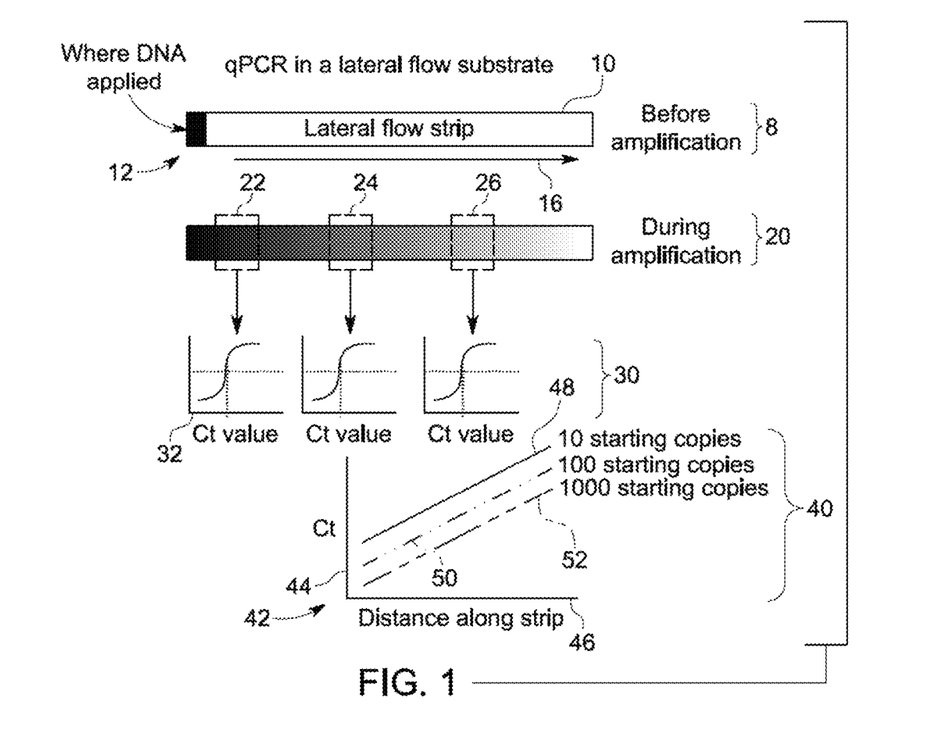
FIG. 1 is a schematic representation of a nucleic acid amplification using a porous substrate according to an embodiment of the disclosure.

To that end, FIG. 1 is a representation of a quantitative amplification technique used in conjunction with a solid amplification substrate, e.g., a porous substrate. As shown in panel 8, a porous substrate 10 may be provided in the form of a lateral flow strip. When a DNA-containing sample (or other nucleic acid sample) is applied to location 12, amplification begins. During amplification, as shown in panel 20, the amplified nucleic acid products flow along arrow 16 and may be detected at a plurality of locations (e.g., locations 22, 24, and 26) at any suitable time point. Based on the magnitude of a detected signal related to an amount of amplified product and the reaction time, the starting copy number may be assessed. For nucleic acids, a starting copy number of a sequence of interest may further be related to particular disease or clinical conditions. For example, an estimated starting copy number above a predetermined threshold may be associated with bacterial or viral infection, cancer diagnosis, presence of a biomarker or sequence of interest in forensic or genotyping assessments, etc. In other embodiments, an estimated starting copy number above a predetermined threshold may be used to determine if an environmental sample is clean or contaminated, e.g., a presence of a non-zero or threshold starting copy number of one or more bacteria types may be indicative of contamination. In yet another embodiment, an estimated starting copy number above a predetermined threshold may be used to determine if a food sample is accurately identified and/or is contaminated. For example, a presence of a particular gene (identified by a non-zero or threshold starting copy number) may be used to determine the species associated with a sample.

In one embodiment, the detected amplification signal may be correlated to starting copy number by correlating the detected signal to a cycle threshold vs. distance for a known sample quantity. The cycle threshold (Ct) is the number of amplification cycles required for a detected signal to cross a predefined threshold. Or, for isothermal amplification, the amount of time required for a detected signal to cross a predefined threshold. Ct is inversely proportional to the amount of target nucleic acid in the sample. Plot 32 is an example of a Ct plot for the time point 22. Plot 42 is a plot of the Ct 44 vs. distance along the strip 46. Each of the plotted lines 48, 50, and 52 correlates to a particular starting copy number. In one embodiment, a sample with an unknown starting copy number may be assessed as provided herein. The detected signal may be plotted using the distance on the porous substrate 10 at which the signal crossed a predetermined threshold and based on a fit to data correlating to a reference sample. The detected signal may also be plotted using the time at which the signal crossed a predetermined threshold at a predetermined distance on the porous substrate 10 and based on a slope and fit to data correlating to a reference sample. Further, the plot may include detected signal at a number of locations along the porous substrate 10.

Figure 2:
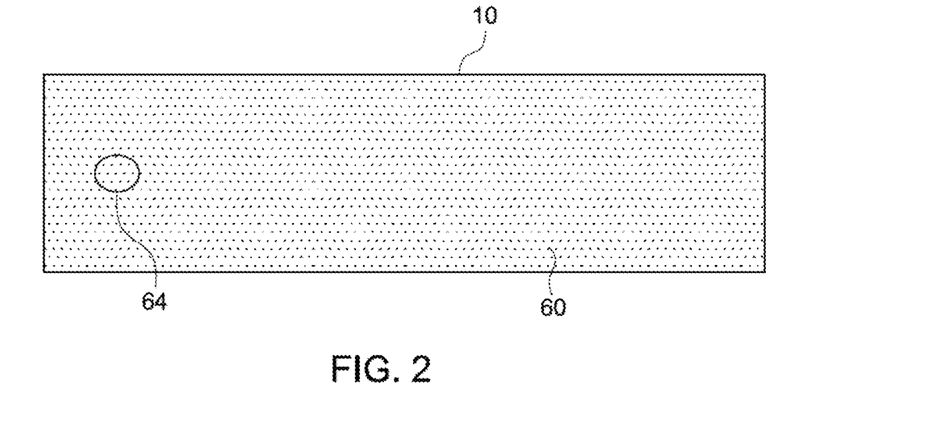
FIG. 2 is a view of a porous substrate according to an embodiment of the disclosure.

FIG. 2 is a view of implementation of a porous substrate 10 in a rectangular strip form. However, it should be understood that the porous substrate 10 may be implemented in any suitable size and shape to facilitate amplification along the porous substrate 10. For example, the porous substrate 10 may be implemented to assess flow along one axis or along multiple axes (e.g., in a star formation). The porous substrate 10 may be formed from any appropriate solid porous material, including paper (e.g., Whatman filter paper), cellulose, porous polymer sheets, glass fibers, quartz fibers, nitrocellulose membranes, etc. In one embodiment, a pore size may be selected based on a predicted size of a desired amplification product. For example, the pore size may be 1-3 microns. Further, in a specific embodiment, the porous substrate 10 may also be formed from a material that is neutral to negatively charged nucleic acids. That is, the material may be selected such that the amplified nucleic acids do not bind or significantly interact with the material of the porous substrate 10. In another embodiment, the porosity may be characterized by the fraction of the volume of voids as over the total volume, e.g., between 0.1 and 1, or 0.25 to 1, where a porosity of 1 is an open channel. Accordingly, the porous substrate 10 may include materials with different areas of porosity as well as materials with open channels.

Figure 3:
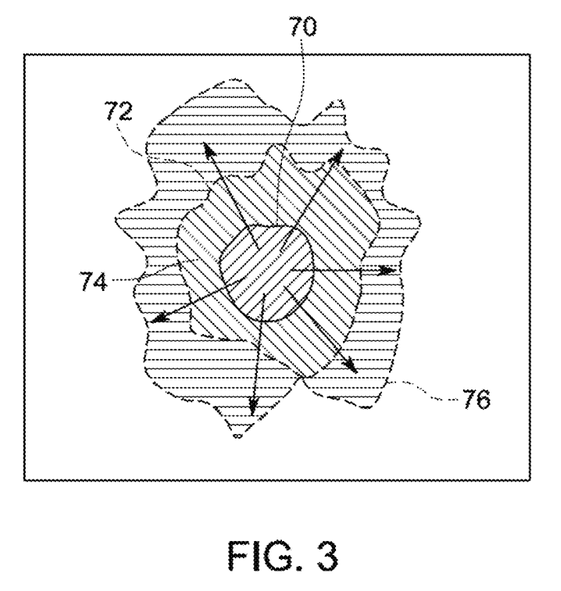
FIG. 3 is a schematic representation of a front of amplification products emanating from a sample application site according to an embodiment of the disclosure.

The porous substrate 10 includes amplification reagents 60 distributed throughout the porous substrate 10. When the sample is applied to an initial location 64 (which may be designated by an index or marker printed or otherwise indicated on the porous substrate 10), the reaction expands outwards, consuming reagents as it progresses. FIG. 3 is a schematic representation of such reaction progression. The sample 70 produces amplified products outward from the application site (e.g. initial location 64) along arrows 72. Over time, a first wavefront 74 forms, and continues to diffuse from the application point. During the reaction, DNA products, H+ ions, pyrophosphate and dyes (if present) may be released while dNTPs and primers are consumed.

In embodiments in which the porous substrate 10 is an elongated strip and the initial location 64 is positioned near an edge of the strip, the amplified product reaches the edges of the porous substrate 10 in many directions in a short time after the reaction starts and after some initial time will only have a net diffusion along the longest axis of the strip. Such an implementation may be advantageous in concentrating the amplification products in a single direction. However, it should be understood that the ability of the amplification reaction to be multidirectional may also be harnessed to yield additional data points. Accordingly, in other embodiments, the initial location 64 may be positioned in a center of a porous substrate 10, which in turn may extend outwardly from the initial location 64 to form a circle or other shape. In addition, the porous substrate 10 may be implemented to test multiple different samples on a single substrate. In such embodiments, the porous substrate 10 may include any number if initial location 64, which may be spaced apart from one another to avoid mixing of multiple reaction fronts.

Figure 4:
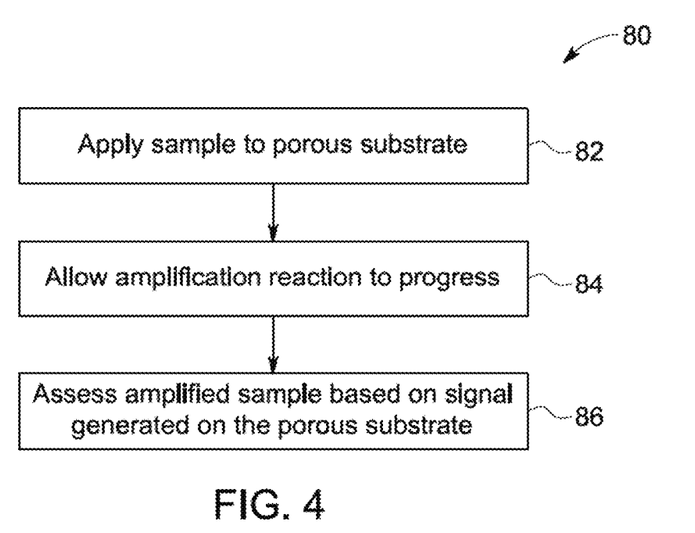
FIG. 4 is a flow diagram of a method of assessing an amplified sample according to an embodiment of the disclosure.

FIG. 4 is a flow diagram of a method 80 of assessing amplification using a porous substrate 10. When the sample is applied to the porous substrate 10, the amplification reaction begins as the nucleic acids contact the appropriate reagents and, in certain embodiments, when other appropriate environmental conditions are present (e.g., activation temperatures for particular reagents). The reaction is allowed to progress for an appropriate amount of time at step 84, and, at one or more selected time points, the amplified sample is assessed based on the position of the signal that is generated by the amplification reaction at step 86. There are multiple ways to measure output from the system, including time-to-distance and distance-at-time. In the first, distance is set and time is measured. In the second, time is set and distance is measured.

Figure 5:
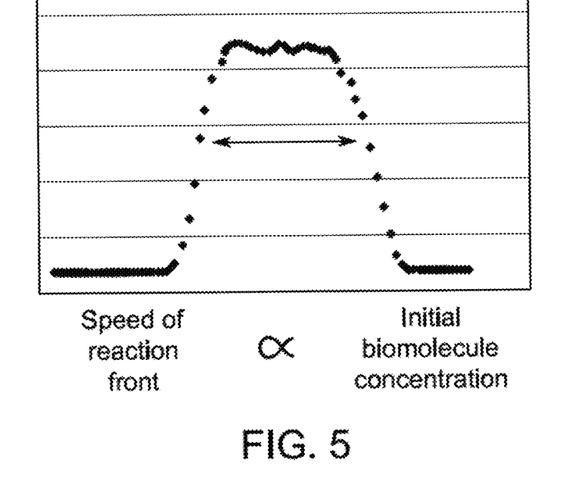
FIG. 5 is a representation of a relationship between a movement of the reaction front and initial concentration

The distance for a set time of the reaction front and the production of amplified products are related to the initial starting copy number of the sequence of interest, as shown in the plot of FIG. 5. Because the porous substrate 10 is generally provided wet or saturated with liquid, the movement of the reaction front is not a wicking or capillary action movement across a dry substrate, but instead is a diffusion of amplified product. The diffusion rate is primarily driven by the continual production of new amplification products from the old ones and, therefore, the movement of the reaction product through the porous substrate 10 is reaction-diffusion, not simply diffusion. That is, because movement is driven by reaction diffusion, the velocity of the reaction front is independent of the starting concentration. The starting concentration determines the "lag time" before the velocity front starts to move. This is different than simple diffusion where speed does depend on the starting concentration. Accordingly, the slope of distance over time is not simply proportional to concentration. However, samples with a known starting copy number may be assessed to determine a characteristic reaction time to distance or distance per time for a reaction in the porous substrate 10. Further, the amplification reagents are distributed generally evenly throughout the porous substrate and in non-limiting concentrations to permit the reaction to progress without reagent bottlenecks as the number of amplified products increases.

Figure 6:
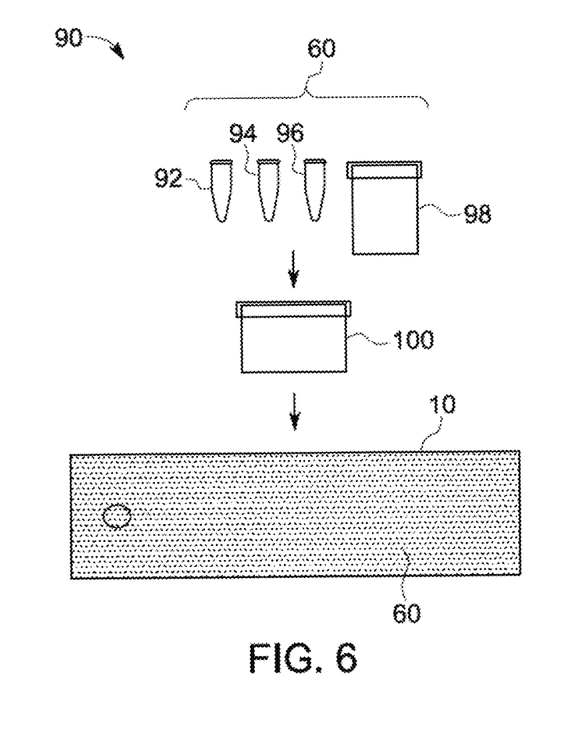
FIG. 6 is a schematic representation of an amplification kit according to an embodiment of the disclosure.

The porous substrate 10 may be provided with or without the amplification reagents 60 in an amplification kit 90 as shown in FIG. 6. The amplification reagents 60 may include one or more primers 92, i.e., oligonucleotides complementary to a target sequence of interest and/or capable of hybridizing to a target sequence of interest. Sequences of interest may include sequences associated with particular pathogens or particular diseases. Further, the primers may include multiple primers specific complementary to different regions of a single desired sequence. The amplification reagents 60 may also include one or more polymerases 94 and nucleotides 96 as well as one or more appropriate buffers 98. The amplification reagents 60 may be selected to work in conjunction with a particular amplification technique (e.g., loop-mediated isothermal amplification, strand displacement amplification, helicase dependent amplification, nicking enzyme amplification reaction). For example, in loop-mediated amplification, 4-6 primers are used that hybridize to 6-8 regions of the target sequence.

In one embodiment, the porous substrate 10 may be provided with the amplification reagents 60 distributed throughout the body of the substrate. For example, the porous substrate 10 may be encapsulated in a packaging that is removed prior to use or coating that prevents evaporation of the amplification reagents 60 during storage. In another embodiment, such a coating may cover the porous substrate with the exception of an opening permitting sample application. For example, the opening may be covered by a removable release liner that is removed to permit the user to apply a sample. Further, it is envisioned that such coatings may be optically transparent or otherwise permeable to the signal generated by the amplification products. In another embodiment, the porous substrate 10 may be provided with the amplification reagents dried on the porous substrate 10. An end user may wet the porous substrate 10 prior to use by soaking the porous substrate 10 in an appropriate buffer.

In another embodiment, the porous substrate 10 may be provided with separate amplification reagents 60 that the end user may apply to the porous substrate 10. In such embodiments, the porous substrate 10 may be provided without any encapsulating coating that may interfere with even application of the amplification reagents 60. To facilitate even distribution of the amplification reagents 60 through the porous substrate 10, the amplification reagents 60 may be first mixed together in a single solution 100 prior to application on the porous substrate 10 rather than being applied separately. The amplification reagents 60 may be provided as separate components or as a premixed solution 100 as part of the amplification kit 90.

In some applications in which the end user desires a porous substrate 10 for testing a particular target sequence, the primers 92 may be provided as part of the amplification kit 90. That is, the amplification kit 90 may be provided with all of the amplification reagents, including primers 92 for a particular target sequence. An end user may purchase the amplification kit 90 that corresponds with a particular disease or clinical condition. In other applications, the primers 92 may be provided separately or provided by the end user. For example, it is envisioned that the porous substrate 10 may be used to assess any target sequence desired by the end user. To that end, the end user may select an appropriate primer set for application to the porous substrate. In such embodiments, the end user may then apply the desired primers 92 to the porous substrate along with the other amplification reagents 60.

Figure 7:
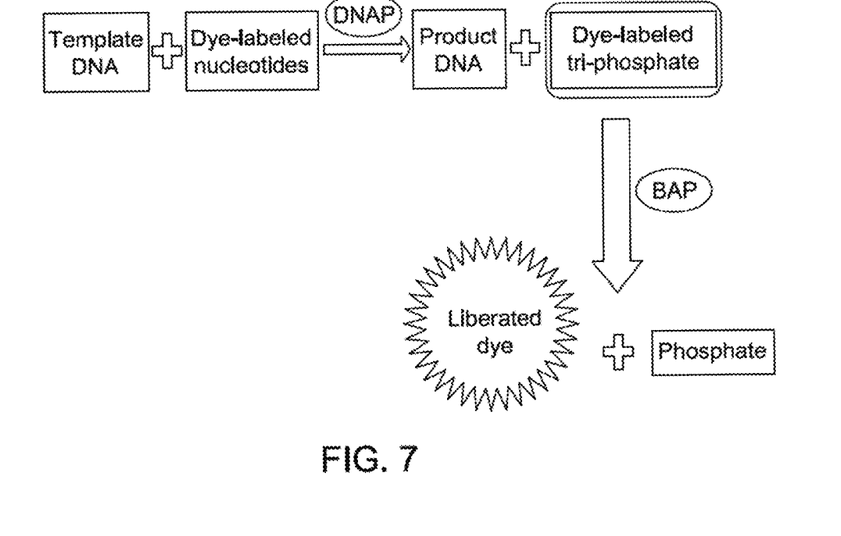
FIG. 7 is a schematic representation of a signal generated by an amplification reaction according to an embodiment of the disclosure.

The amplified products of the reaction may be detected by measuring signals from detectable moieties generated by the amplification. For example, detection may involve measuring the concentration of one of the reaction products directly (e.g. amplicons, H+, pyrophosphate, etc) or by measuring something released from the nucleotides upon incorporation into the amplified DNA (etc a dye). This information can be used to track the movement of the reaction/diffusion gradient front. Accordingly, the amplification reagents 60 may include one or more appropriate signal molecules that are capable of providing a detectable signal using one or more detection techniques (e.g., spectrometry, calorimetry, spectroscopy, visual inspection, or any other detection method). Suitable examples of a detectable signal may include a visible signal, an optical signal, an electrical signal, an electrochemical signal, or a radioactive signal. In one embodiment, shown in FIG. 7, DDAO labeled deoxynucleoside tetraphosphates (dNTPs) are utilized to perform quantitative measurements of amplification. In one embodiment, such nucleotide substrates are radiolabeled or have attached thereto some other type of label or dye, radioactive isotopes, fluorescent molecules, phosphorescent molecules, enzymes, antibodies, probes, stains, and ligands. Examples of detection labels that can be incorporated into amplified DNA include nucleotide analogs and nucleotides modified with biotin or with suitable haptens such as digoxygenin. It should be understood that one or more of the provided nucleotides 94 may be labeled. In a specific example, as shown in FIG. 7, the nucleotides 94 may be labeled with a signal molecule such as a dye. When the nucleotides 94 are incorporated into an amplification product, the dye is released from the nucleotide to yield a dye-labeled triphosphate, which in turn is liberated after reaction with a phosphatase to yield liberated dye. The dye may be detected once liberated depending on the characteristics of the dye (e.g. via optical, visible, and/or electrical techniques). In specific embodiments, signal molecules may be assessed via pyrophosphate detection, electrochemical detection of H+, intercalating electrochemical probes, redox active dyes, pyrophosphate, intercalating dyes, or nucleotide dyes.

Examples of signal molecules that may be used in conjunction with the disclosed embodiments include, for example, a chromophore, a fluorophore, a Raman-active tag, a radioactive label, an enzyme, an enzyme substrate, or combinations thereof. As stated above, with regard to labeled nucleotides, the signal molecule and the nucleotides 94 may be present in a single entity (e.g., a target binding protein with a fluorescent label or radiolabel). In other embodiments the nucleotides 94 and signal molecules are discrete entities that associate with each other prior to or upon introduction to the porous substrate 10. A signal molecule may provide a characteristic signal following interaction with an energy source or a current, such as an electromagnetic radiation source or a fluorescence excitation source. Electromagnetic radiation source may be capable of providing electromagnetic energy of any wavelength including visible, infrared, and ultraviolet. Electromagnetic radiation may be in the form of a direct light source or may be emitted by a light emissive compound such as a donor fluorophore. A fluorescence excitation source may be capable of making a source fluoresce or may give rise to photonic emissions (that is, electromagnetic radiation, directed electric field, temperature, physical contact, or mechanical disruption). Suitable signal generators may provide a signal capable of being detected by a variety of methods including optical measurements (for example, fluorescence), electrochemical signal, electrical conductivity, or radioactivity. Suitable signal molecules may be, for example, light emitting, energy accepting, fluorescing, radioactive, redox active, or quenching.

Figure 8:
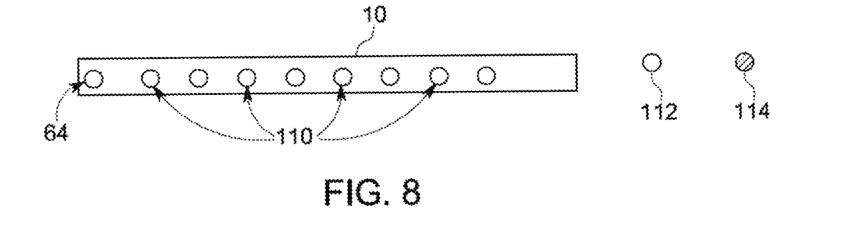
FIG. 8 is a view of a porous substrate including threshold markers at various distances from an initial sample location according to an embodiment of the disclosure.

FIG. 8 is an example of a porous substrate 10 including a plurality of assessment locations 110 spaced apart along an axis and from the initial location 64. The locations 110 may be indicated by pre-printed markers. In embodiments in which the assessment is colorimetric, an unfilled location 112 corresponds to amplification below a threshold while a filled location 114 corresponds to levels above a threshold.

Figure 9:
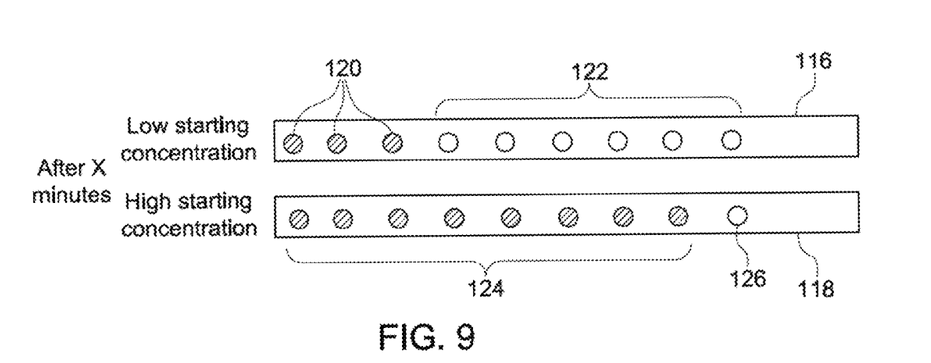
FIG. 9 is a representative comparison between distance of amplified products for different starting material concentrations.

FIG. 9 shows an assessment using two such porous substrates 10, each with a different amount of starting material. For a lower concentration of starting material, the test 116 shows three filled marker locations 120 and six unfilled locations 122. For the higher concentration test 118, after the same amount of time (i.e., time x), eight locations 124 are filled while one location 126 is unfilled. In embodiments in which the test is colorimetric or otherwise visible (e.g., under a fluorescent light), the number of filled and unfilled locations at time x may be correlated to a particular starting concentration. In such embodiments, the amplification kit 90 may be provided with comparison graphs and tables to indicate an estimated concentration at time point x with all possible combinations of filled/unfilled locations 110. Accordingly, the porous substrate 10 may provide a rapid and easy to use assessment of not only a presence of a particular target sequence, but also an estimated amount, i.e., a quantitative assessment of nucleic acids in the initial sample. Further, such a technique may also be implemented with automatic detection.

Instead of monitoring intensity over time, measuring when the signal at different points goes above a threshold permits a wide dynamic range of quantification even using a signal molecule/detector without a wide dynamic range. That is, by introducing distance and time variables to determine what the "Ct" value at different distances from the starting point, the dynamic range of the system is expanded. Further, the detector is binary rather than having to be calibrated for each testing instance. In particular, the dynamic range of the detector is determined by the number of detection points and their distance apart rather than an inherent range of the detector itself. In this manner, a detector that is even binary in range may used in conjunction with distance and time information to be configured to provide a wide dynamic range.

Figure 10:
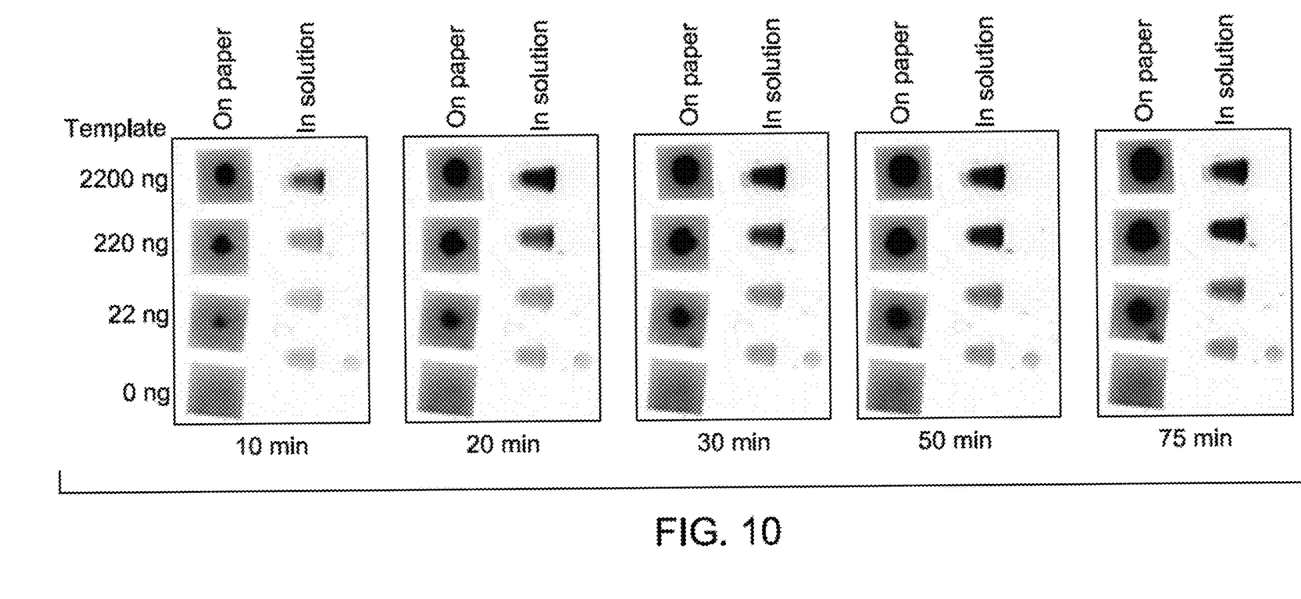
FIG. 10 shows a comparison between detected signals of amplified genomic DNA at different reaction times and a various starting concentrations on a porous substrate and in solution.

FIG. 10 shows a comparison between gradients formed with a porous substrate 10 vs. a solution-based technique. Genomic DNA of various concentrations was assessed at various concentrations and at multiple time points. A gradient is formed in a paper substrate when comparing the size of the detected spots for a particular concentration over time while the solution-based technique does not form such a gradient. For example, for the 22 ng sample, the gradient continues to grow over the time points, indicating that a heterogeneous gradient is formed. In one embodiment, a desired test may be calibrated by determining in which concentration ranges and at what time points a gradient is formed.

In another example, an experiment was performed with a dried cellulose substrate whose surface was previously blocked with bactopeptone. The substrate was saturated with amplification reagent mix for DNA amplification (IsoAmp III Universal tHDA kit from Biohelix). The mix included all components (enzymes, buffers, nucleotides, primers, etc) excluding DNA template. The primers were designed for *mycobacterium tuberculosis* (TB) template. Purified TB DNA was added to position 0. Two different DNA amounts were used: 5 ng or 500 pg.

The substrate was incubated at 65° C. for various times. After 8 or 24 hours of incubation, the substrate was removed from incubator and cut into 2-3 mm segments. The fluid was extracted from the segments via centrifugation and analyzed on a 15% TBE-Urea polycrylamide gel using gel electrophoresis. The concentration of amplified DNA in each segment was determined from gel image.

The results of the experiment are shown below in Table 1. The results show that at each time, the farthest distance traveled is higher for higher concentration. In particular, Table 1 shows a farthest distance at which at least a minimum amount of DNA is detected (e.g., detection above a threshold).

TABLE 1

| Starting amount of TBDNA | Time | Farthest distance where at least 0.08 ng/μL was detected |
|---|---|---|
| 5 ng | 8 hr | 5 mm |
| 500 pg | 8 hr | 2 mm |
| 5 ng | 24 hr | 9 mm |
| 500 pg | 24 hr | 5 mm |

Figure 11:
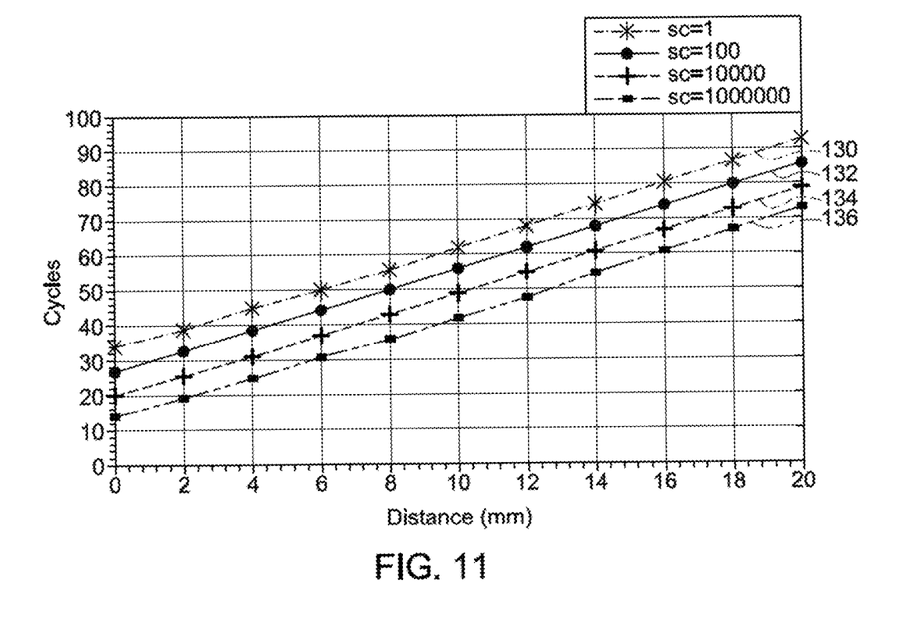
FIG. 11 shows a representative plot of distance of amplified products vs. time on a porous substrate for different starting copy numbers.

FIG. 11 is a plot of predicted threshold value at time (e.g., cycles) vs. distance on a porous substrate 10 from sample application for four different starting copy numbers represented by lines 130, 132, 134, and 136. The line of the highest concentration of starting copy, line 136, reaches the threshold sooner than the other samples.

Figure 12:
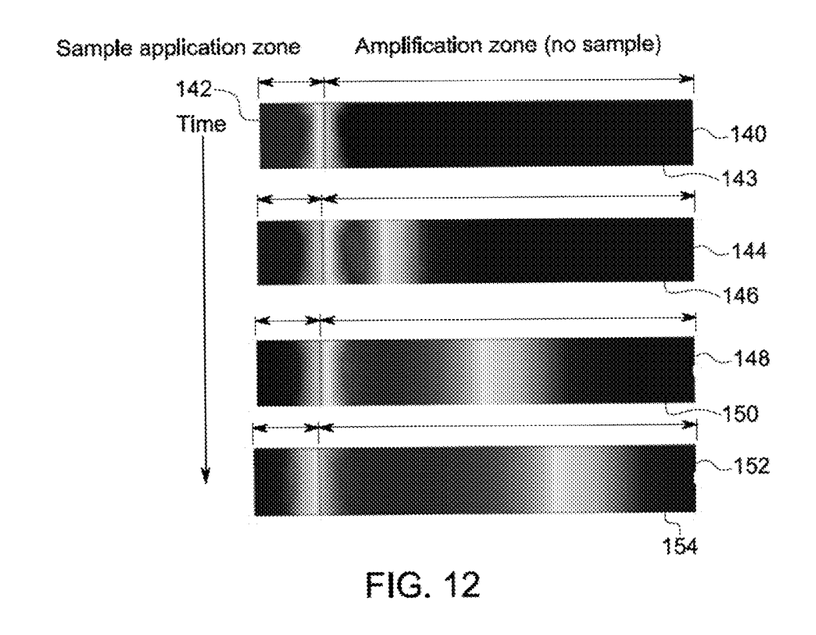
FIG. 12 shows 2D simulation data of an amplification front on a porous substrate.

FIG. 12 is 2D simulation data showing areas above the threshold as a function of time for a sample applied to a porous substrate 10 as provided. In panel 140 the sample at 142 is above threshold and, as time progresses (e.g., shown in panels 144, 148, and 152), the area above the threshold (e.g., areas 146, 148, and 154) moves along the porous substrate 10. An additional advantage of the diffusion-based technique disclosed herein is that diffusion of the amplified products is related to reaction time for amplification. In contrast, any sample contaminants diffuse independently of amplification and ahead of the reaction front. Accordingly, the disclosed techniques may be used with relatively heterogeneous or complex samples, such as unprocessed bodily fluids.

Figure 13:
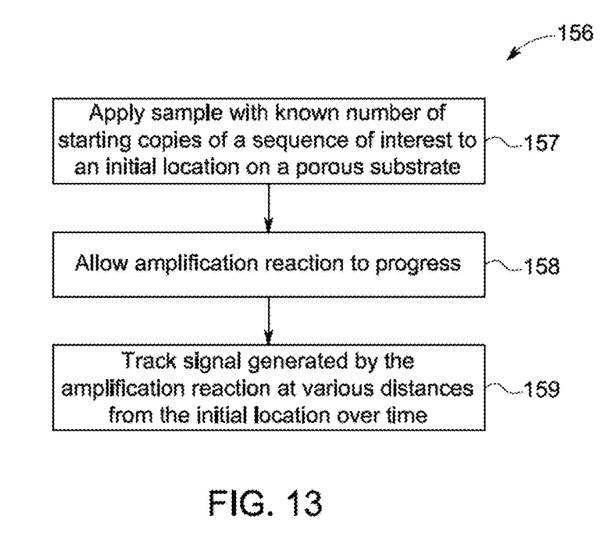
FIG. 13 is a flow diagram of a technique for calibrating a porous substrate according to an embodiment of the disclosure.

FIG. 13 is a flow diagram of a method 156 for calibrating a nucleic acid quantification. At step 157, a calibration may be performed by applying a known sample (e.g., with a known concentration or copy number of a target sequence) to an initial location on a porous substrate and the amplification reaction is allowed to progress for at least one time point at step 158. A signal at a plurality of distances and at a plurality of time points is detected at step 159. By providing at least one plot correlating distance at a set time to known copy number, a user may determine a concentration of an unknown sample. Alternatively, a time to reach a particular distance (e.g., a time at which the sample reaches a distance with a concentration of reaction product above a threshold) may also be correlated to a starting copy number. In other embodiments, the calibration method 156 is performed for multiple concentrations to provide additional calibration data.

Figure 14:
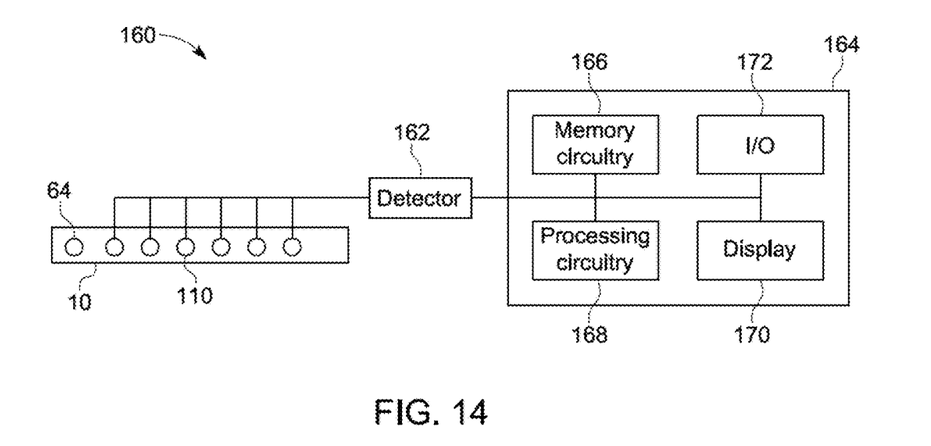
FIG. 14 is an illustration of an amplification system according to an embodiment of the disclosure.

Such calibration data may be stored in a processor-based device so that quantification is performed automatically. For example, as shown in FIG. 14, the techniques disclosed herein may be used in conjunction with a system 160 that includes one or more sensors or detectors 162 for detecting the signal generated by the amplification reaction and coupled to an assessment device 164. The detector 162 may be configured to detect one or more signal molecules. For example, in certain embodiments, the detector 162 may be configured to detect optical or electrochemical signals. The porous strip 10 may couple to the detector 162 to facilitate detection at one or more locations 110 along the substrate 10. The system 160 may also include elements for heating the porous strip to activate amplification. For example, the amplification reagents 60 may be configured to react at particular temperatures or using particular temperature cycles. Accordingly, the system 160 may be configured to provide cyclical or isothermal heating to the porous substrate 10.

The system 160 may also include computer-readable memory circuitry 166, such as magnetic, electronic, or optical storage media, for storing programs and routines executed by the device 164. The stored programs or routines may include programs or instructions for performing all or part of the present techniques. The system 160 may also include processing circuitry 168 for executing the programs or instructions. The device 164 may also include various input/output (I/O) interfaces 172, as well as various network or communication interfaces to allow communication with user interface devices, such as a display 170, that may be used for viewing and inputting quantification information. The various network and communication interfaces may allow connection to both local and wide area intranets and storage networks as well as the Internet. The various I/O and communication interfaces may utilize wires, lines, or suitable wireless interfaces, as appropriate or desired.

Technical effects of the disclosed embodiments include rapid nucleic acid amplification and assessment with an improved dynamic range and no active movement of amplified material off of a testing substrate. That is, the porous substrate facilitates amplification and detection in a single step.

This written description uses examples, including the best mode, and also to enable any person skilled in the art to practice the disclosed embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of assessing amplification of nucleic acids comprising:
   providing a lateral flow strip comprising a porous substrate and comprising a plurality of amplification reagents distributed throughout the body of the porous substrate, wherein the amplification reagents comprise nucleotides, one or more nucleic acid primers for a nucleic acid sequence of interest, and amplification enzymes;

applying a sample having the nucleic acid sequence of interest to a predetermined initial location on the lateral flow strip at an initial time;

allowing the sample to react with the amplification reagents in the lateral flow strip at the initial location for a predetermined duration of time to generate amplification products of the nucleic acid sequence of interest, wherein amplification products comprise one or more detectable moieties configured to provide a visible signal on the lateral flow strip when the amplification products are generated during amplification and wherein the amplification products and the visible signal move outwards on the lateral flow strip from the initial location during amplification;

determining a distance between a farthest location relative to the predetermined initial location of the visible signal on the lateral flow strip at an end of the predetermined duration of time, wherein the farthest location is spaced apart from the initial location by the distance; and determining a starting copy number of the nucleic acid sequence of interest in the sample using a plot or table showing a relationship between a plurality of farthest distances and a corresponding plurality of control samples having known copy numbers of the nucleic acid sequence of interest.

2. The method of claim 1, wherein the porous substrate comprises a printed marker corresponding to the initial location and a plurality of printed markers corresponding to different distances from the initial location.

3. The method of claim 1, wherein the amplification reagents comprise isothermal nucleic acid amplification reagents.

4. The method of claim 1, wherein the amplification reagents comprise DNA polymerase and one or more nucleic acid primers.

5. The method of claim 1, wherein the amplification reagents comprise RNA polymerase.

6. The method of claim 1, comprising determining that the sample does not contain a threshold amount of the sequence of interest if the detected signal does not reach a minimum distance from the initial location.

7. The method of claim 1, comprising determining a clinical characteristic of a patient from whom the sample was taken based on the initial concentration of the nucleic acid sequence of interest in the sample, wherein the clinical characteristic is associated with a presence or absence of the nucleic acid sequence of interest and wherein the amplification reagents comprise one or more primers complementary to the nucleic acid sequence of interest.

8. The method of claim 1, wherein the porous substrate is saturated with liquid.

9. The method of claim 1, wherein liquid moves through the substrate during amplification.

10. The method of claim 1, wherein providing the porous substrate comprises applying the amplification reagents to the porous substrate in a single solution.

11. The method of claim 1, comprising heating the porous substrate to activate one or more of the amplification reagents.

12. The method of claim 11, wherein the heating is to an isothermal temperature.

13. The method of claim 1, wherein the signal comprises a visible signal and/or a fluorescent signal.

14. The method of claim 1, wherein the signal comprises an electrochemical signal or a pH change.

15. The method of claim 1, wherein the porous substrate has a non-uniform porosity.

16. The method of claim 15, wherein the porous substrate comprises an open channel with a porosity of one.

17. The method of claim 1, wherein the signal is generated by release of a dye.

18. The method of claim 1, wherein the signal is generated by one or more of amplicons, $H^+$, or pyrophosphate.

19. The method of claim 1, wherein the amplification reagents are distributed generally evenly throughout the body of the porous substrate.

20. The method of claim 1, wherein the initial location is on or near an edge of the lateral flow strip.

21. The method of claim 1, wherein the visible signal is generated by production of a labeled triphosphate from dye-labeled nucleotides of the amplification reagents and liberation of the dye by reaction with a phosphatase.

22. The method of claim 1, wherein the starting copy number is determined based on the control sample whose furthest distance is closest to the furthest distance of the sample.

23. The method of claim 1, wherein the relationship is driven by reaction diffusion and not wicking.

* * * * *